US006132699A

United States Patent [19]
Bernstein et al.

[11] Patent Number: 6,132,699
[45] Date of Patent: *Oct. 17, 2000

[54] MICROENCAPSULATED FLUORINATED GASES FOR USE AS IMAGING AGENTS

[75] Inventors: Howard Bernstein, Cambridge; Julie Ann Straub, Winchester; Henry T. Brush, Somerville; Richard E. Wing, Cambridge, all of Mass.

[73] Assignee: Acusphere, Inc., Cambridge, Mass.

[*] Notice: This patent is subject to a terminal disclaimer.

[21] Appl. No.: 09/158,295

[22] Filed: Sep. 22, 1998

Related U.S. Application Data

[63] Continuation of application No. 08/745,676, Nov. 8, 1996, Pat. No. 5,853,698, which is a continuation of application No. 08/611,248, Mar. 5, 1996, Pat. No. 5,611,344.

[51] Int. Cl.[7] .................................................. A61B 8/13
[52] U.S. Cl. ............................................................ 424/9.52
[58] Field of Search ................................... 424/9.52, 489, 424/490, 493, 497, 501; 600/431, 458

[56] References Cited

U.S. PATENT DOCUMENTS

| | | | |
|---|---|---|---|
| 4,265,251 | 5/1981 | Tickner | 128/660 |
| 4,276,885 | 7/1981 | Tickner et al. | 128/660 |
| 4,442,843 | 4/1984 | Rasor et al. | 128/660 |
| 4,466,442 | 8/1984 | Hilmann et al. | 128/653 |
| 4,533,254 | 8/1985 | Cooke et al. | 366/176 |
| 4,544,545 | 10/1985 | Ryan et al. | 424/9.52 |
| 4,572,203 | 2/1986 | Feinstein | 128/661 |
| 4,637,905 | 1/1987 | Gardner et al. | 264/4.3 |
| 4,657,756 | 4/1987 | Rasor et al. | 424/9.52 |
| 4,681,119 | 7/1987 | Rasor et al. | 128/660 |
| 4,684,479 | 8/1987 | D'Arrigo | 252/307 |
| 4,718,433 | 1/1988 | Feinstein | 128/660 |
| 4,757,128 | 7/1988 | Domb et al. | 528/271 |
| 4,774,958 | 10/1988 | Feinstein | 424/9.52 |
| 4,789,724 | 12/1988 | Domb et al. | 528/176 |
| 4,844,882 | 7/1989 | Widder et al. | 424/9.52 |
| 4,857,311 | 8/1989 | Domb et al. | 424/78 |
| 4,859,363 | 8/1989 | Davis et al. . | |
| 4,865,836 | 9/1989 | Long | 424/5 |
| 4,888,176 | 12/1989 | Langer et al. | 424/426 |
| 4,985,550 | 1/1991 | Charpoit et al. . | |
| 4,987,154 | 1/1991 | Long | 514/772 |
| 4,993,415 | 2/1991 | Long . | |
| 5,077,036 | 12/1991 | Long | 424/9 |
| 5,078,146 | 1/1992 | Sato | 128/661.08 |
| 5,080,885 | 1/1992 | Long | 424/5 |
| 5,088,499 | 2/1992 | Unger . | |
| 5,107,842 | 4/1992 | Levine et al. | 128/662.02 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor et al. | 424/2 |
| 5,145,684 | 9/1992 | Liversidge et al. | 424/489 |
| 5,147,631 | 9/1992 | Glajch et al. | 424/9.5 |
| 5,149,319 | 9/1992 | Unger . | |
| 5,155,215 | 10/1992 | Ramney | 534/16 |
| 5,171,755 | 12/1992 | Kakufman | 514/749 |

(List continued on next page.)

FOREIGN PATENT DOCUMENTS

| | | |
|---|---|---|
| 76144/91 | 11/1991 | Australia . |
| 092 918 A1 | 11/1983 | European Pat. Off. . |
| 166 596 | 1/1986 | European Pat. Off. . |
| 231 091 A1 | 8/1987 | European Pat. Off. . |
| 245 019 A2 | 11/1987 | European Pat. Off. . |
| 324 938 B1 | 6/1988 | European Pat. Off. . |
| 295 055 A1 | 12/1988 | European Pat. Off. . |
| 307 087 A1 | 3/1989 | European Pat. Off. . |
| 359 246 A2 | 3/1990 | European Pat. Off. . |
| 467 031 A2 | 1/1992 | European Pat. Off. . |
| 502 814 A2 | 9/1992 | European Pat. Off. . |
| 512 693 | 11/1992 | European Pat. Off. . |
| 535 387 | 4/1993 | European Pat. Off. . |
| 554 213 A1 | 8/1993 | European Pat. Off. . |
| 398 935 | 8/1994 | European Pat. Off. . |
| 681 843 | 1/1996 | European Pat. Off. . |
| 619 743 | 1/1997 | European Pat. Off. . |
| 804 932 | 11/1997 | European Pat. Off. . |
| 644 777 | 2/1998 | European Pat. Off. . |
| 19510690 | 9/1996 | Germany . |
| WO 80/02365 | 11/1980 | WIPO . |
| WO 89/06978 | 8/1989 | WIPO . |
| WO 89/10118 | 11/1989 | WIPO . |
| WO 90/01952 | 3/1990 | WIPO . |
| WO 91/02560 | 2/1992 | WIPO . |

(List continued on next page.)

OTHER PUBLICATIONS

Allen & Hansen, "Pharmacokinetics of Stealth Versus Conventional Liposomes: Effect of Dose", *Biochimica et Biophysics Acta* 1068, 133–141 (1991).

Allen, et al., "Liposomes Containing Synthetic Lipid Derivatives of Poly(ethylene glycol) Show Prolonged Circulation Half–Lives in Vivo", *Biochimica et Biophysica Acta*, 1066, 29–36 (1991).

American Heart Association, *Abstracts of the 58th Scientific Sessions,* Circulation 72: Oct. 1985 III–427.

Association of University Radiologists, Association of University Radiologists Proceedings of Annual Meeting, *Journal of Clinical and Laboratory Research Investigative Radiology* 17:4, Abstract 110 (1982).

Beck, et al., "A New Long–Acting Injectable Microcapsule System For The Administration of Progesterone", *Fertility and Sterility,* 31(5):545–551 (1979).

(List continued on next page.)

*Primary Examiner*—Gary E. Hollinden
*Attorney, Agent, or Firm*—Arnall Golden & Gregory, LLP

[57] ABSTRACT

It has been discovered that the incorporation of fluorinated gases, especially a perfluorocarbon such as octafluoropropane, into synthetic polymeric microparticles, significantly enhances echogenicity as compared with microparticles having air incorporated therein. The microencapsulated perfluorocarbon is manufactured with a diameter suitable for the targeted tissue to be imaged, for example, for intravenous or oral administration. In one embodiment, bioadhesive microparticles are formed for enhanced imaging of mucosal surfaces.

21 Claims, No Drawings

U.S. PATENT DOCUMENTS

| | | |
|---|---|---|
| 5,209,720 | 5/1993 | Unger . |
| 5,228,446 | 7/1993 | Unger .................................... 424/9.51 |
| 5,230,882 | 7/1993 | Unger ......................................... 424/9 |
| 5,334,381 | 8/1994 | Unger ......................................... 424/9 |
| 5,344,393 | 9/1994 | Roth . |
| 5,352,435 | 10/1994 | Unger . |
| 5,362,478 | 11/1994 | Desai et al. ................................. 424/9 |
| 5,393,524 | 2/1995 | Quay ......................................... 424/9 |
| 5,413,774 | 5/1995 | Schneider et al. ..................... 424/9.51 |
| 5,496,535 | 3/1996 | Kirkland ............................... 424/9.37 |
| 5,501,863 | 3/1996 | Rossling et al. ....................... 424/9.52 |
| 5,527,521 | 6/1996 | Unger ....................................... 424/93 |
| 5,529,766 | 6/1996 | Klaveness et al. .................... 424/9.52 |
| 5,547,656 | 8/1996 | Unger ...................................... 424/9.4 |
| 5,558,854 | 9/1996 | Quay ..................................... 424/9.52 |
| 5,565,215 | 10/1996 | Gref et al. . |
| 5,567,413 | 10/1996 | Klaveness ............................. 424/9.51 |
| 5,573,751 | 11/1996 | Quay ..................................... 424/9.52 |
| 5,578,292 | 11/1996 | Schneider et al. ..................... 424/9.51 |
| 5,585,112 | 12/1996 | Unger et al. ............................ 424/450 |
| 5,618,514 | 4/1997 | Schroder ................................ 424/9.5 |
| 5,686,060 | 11/1997 | Schneider et al. . |
| 5,955,143 | 9/1999 | Wheatley ............................ 427/213.3 |

FOREIGN PATENT DOCUMENTS

| | | |
|---|---|---|
| WO 92/05806 | 4/1992 | WIPO . |
| WO92/08496 | 5/1992 | WIPO . |
| WO 92/11873 | 7/1992 | WIPO . |
| WO 92/15284 | 9/1992 | WIPO . |
| WO 92/17212 | 10/1992 | WIPO . |
| WO 92/18164 | 10/1992 | WIPO . |
| WO92/17213 | 10/1992 | WIPO . |
| WO92/18165 | 10/1992 | WIPO . |
| WO 92/19272 | 11/1992 | WIPO . |
| WO 92/21382 | 12/1992 | WIPO . |
| WO 92/22298 | 12/1992 | WIPO . |
| WO 93/00930 | 1/1993 | WIPO . |
| WO 93/01798 | 2/1993 | WIPO . |
| WO 93/05819 | 4/1993 | WIPO . |
| WO 93/06869 | 4/1993 | WIPO . |
| WO 93/07905 | 4/1993 | WIPO . |
| WO 93/10440 | 5/1993 | WIPO . |
| WO 93/17718 | 9/1993 | WIPO . |
| WO 93/25242 | 12/1993 | WIPO . |
| WO 94/02122 | 2/1994 | WIPO . |
| WO 94/09829 | 5/1994 | WIPO . |
| WO 94/16739 | 8/1994 | WIPO . |
| WO 94/19101 | 9/1994 | WIPO . |
| WO 94/21301 | 9/1994 | WIPO . |
| WO 94/21302 | 9/1994 | WIPO . |
| WO 94/21303 | 9/1994 | WIPO . |
| WO 95/03357 | 2/1995 | WIPO . |
| WO 95/06518 | 3/1995 | WIPO . |
| WO 95/23615 | 9/1995 | WIPO . |
| WO 95/32006 | 11/1995 | WIPO . |
| WO 96/04018 | 2/1996 | WIPO . |
| WO 96/18420 | 6/1996 | WIPO . |
| WO 96/28191 | 9/1996 | WIPO . |
| WO 96/38181 | 12/1996 | WIPO . |
| WO 96/40277 | 12/1996 | WIPO . |
| WO 97/22409 | 6/1997 | WIPO . |

OTHER PUBLICATIONS

Benita, et al., "Characterization of Drug–Loaded Poly(d, l–lactide) Microspheres", *J. Pharmaceutical Sciences*, 73(12):1721–1724 (1984).

Bleecker, H., et al., "On the Application of Ultrasonic Contrast Agents for Blood Flowmetry and Assessment of Cardiac Perfusion", *Journal of Ultrasound in Medicine*, 9:461–471 (1990).

Bleecker, H., et al., "Ultrasonic Characterization of Albunex, A New Contrast Agent", *Journal Acoustical Society of America*, 87:1792–1797 (1990).

Burns "Mezzi Di Contrasto Per Ecografia Nella Diagnostic Radiologic", *La Radiologic Medica–Radiol Med.*, 87(Supple, 1 al, n 5):71–82 (1994).

Carroll, et al., "Gelatin Encapsulated Nitrogen Microbubbles As Ultrasonic Contrast Agents", *Invest. Radiol.*, 15:260–266 (1980).

Carroll, et al., "Ultrasonic Contrast Enhancement Of Tissue By Encapsulated Microbubbles[1]", *Radiology*, 143:747–750 (1982).

Davis, P. L., et al., "Echogenicity Cause By Stable Microbubbles in a Protein–Lipid Emulsion", *The Journal of Clinical Ultrasound*, 9:249–252, Jun. 1981.

De Jong, N., et al., "Absorption and Scatter of Encapsulated Gas Filled Micropsheres: Theoretical Considerations and Some Measurements", *Ultrasonics*, 30:95–103 (1992).

DeJong and Cate, "New Ultrasound Contrast Agents and Technological Innovations," *Ultrasonics* 34(2–5):587–590 (1996).

Deng, et al., "Synthesis And Characterization Of Block Copolymers From D,L–Lactide And Poly(Ethylene Glycol) With Stannous Chloride", *J. Of Polymer Science: Part C: Polymer Letters*, 28:411–416 (1990).

Feinstein, et al., "Contrast Echocardiography During Coronary Arteriography in Humans: Perfusion and Anatomic Studies", *J. Am. Coll. Cardiol.*, 11:59–65 (1988).

Feinstein, Steven B., et al., "Safety and Efficacy Of A New Transpulmonary Ultrasound Contrast Agent: Initial Multicenter Clinical Results," *Journal of American College of Cardiology*, 16:316–324, Aug. 1990.

Feinstein, Steven B., et al., "Microcardial Contrast Echocardiography: Examination of Infracoronary Injections. Microbubble Diameters And Video Intensity Decay," *American Journal of Physilogic Imaging* 1:12–18 (1986).

Fobbe, V. F., et al, "Farbkodierte Duplexsonographie Un Ultraschallkontrastmittel–Nachweis Von Renalen Perfusionsdefekten Im Tierexperiment", *Fortschr. Röntgenstr.* 154:242–245 (1991).

Fritzsch, et al., "SH U 508, A Transpulmonary Echocontrast Agent", *Invest. Radiol.*, 25(Suppl 1):160–161 (1990).

Fritzsch, et al., "Preclinical And Clinical Results With An Ultrasonic Agent", *Invest. Radiol.*, 23(Suppl 1):302–305(1988).

Gardner et al., "A Survey of Intraocular Gas Use in North America", *Arch. Ophthalmol.* 106:1188–9 (1988).

Gottlieb, S. et al., *J. Am. Soc. Echo.*, 8:328 (1995).

Handa, T., et al., "Phospholipid Monolayers at the Triolein–Saline Interface: Production of Microemulsion Particles and Conversion of Monolayers to Bilayers", *Bicohemistry* 29:2884–2890 (1990).

Ikada et al., *Chem. Abstracts*, 125(10), abs. No. 123787 (Sep. 2, 1996).

Illum & Davis, "The Organ Uptake of Intravenously administered Colloidal Particles Can Be Altered Using A Non–Ionic Surfactant (Poloxamer 338)", *FEBS Lett.*, 167:79–82(1984).

Jacobs, "Intraocular gas measurement using A–scan Ultrasound", *Current Eye Research* 5(8):575–8 (1986).

Kabalnov, A. S., et al., "Safety and Efficacy of a New Transpulmonary Ultrasound Contrast Agent: Initial Multicenter Clinical Results", *Journal of Fluorine Chemistry* 50:271–284 (1990).

Lasic, et al., "Sterically Liposomes*: A Hypothesis On The Molecular Origin Of The Extended Circulation Times", *Biochimica et Biophysics Acta*, 1070:87–192(1991).

Marshall, Nissim, *Encyclodedie Des Gaz, Encyclopedia of Gas* (1976).

Maruyama, et al., "Effect Of Molecular Weight In Amphipathic Polyethyleneglycol On Prolonging The Circulation Time Of Large Unilamellar Liposomes", *Chem. Pharm. Bull.*, 39(6):1620–1622(1991).

Mathiowitz, et al., "Novel Microcapsules For Delivery Systems", *Reactive Polymers*, 6:275–283(1987).

Mattrey, Robert F., et al., "Perfuorctylbromide: A Liver/Spleen–Specific and Tumor–Imaging Ultrasound Contrast Material", *Radiology* 145:759–762, Dec. 1982.

Meltzer, R., et al., "Transmission of Ultrasonic Contrast Through the Lungs," *Ultrasound in Medicine and Biology*, 7(4):377–384 (1981).

Meltzer, et al., "Why do the Lungs Clear Ultrasonic Contrast?", *Ultrasound In Medicine & Biology*, 6:263–269 (1980).

Nomura et al., "US Contrast Enhancement of Hepatic Tumor with Helium Gas Microbubbles: A Preliminary Report", *Jpn J. Med. Ultrasonics*, 18(5): 28 (1991).

Ohta, T., et al., "Effect of the Contrast Agent and the Agitation Method on the Size, Number and Stability of Microbubbles: A Basic Experiment for the Myocardial Contrast Study", *Japanese Journal of Medical Ultrasonics* 18:318–325 (1991).

Ophir, J., et al., "Contrast Agents In Diagnostic Ultrasound," *Ultrasound in Medicine and Biology* 15:319–333 (1989).

Parker, et al., "Attenuation of Ultrasound Magnitude and Frequency Dependence for Tissue Characterization", *Radiology*, 153(3):785–788(1984).

Parker & Wang, "Measurement of Ultrasonic Attenuation Within Regions selected from B–Scan Images", IEEE Trans. Biomed. Enar. BME, 30(8):431–437(1983).

Parker, et al., "A Particulate Contrast Agent with Potential for Ultrasound Imaging of Liver", *Ultrasound in Medicine & Biology*, 13(9):555–561(1987).

Rovai, et al., "Contrast Echo Washout Curves From The Left Ventricle: Application Of Basic Principles Of Indicator–Dilution Theory And Calculation Of Ejection Fraction", *J. Am. Coll. Cardiol.*, 10:125–134(1987).

Sato, et al., "Porous Biodegradable Microspheres for Controlled Drug Delivery. I. Assessment of Processing Conditions and Solvent Removal Techniques," *Pharmaceutical Research* 5(1):12–30 (1988).

Schlief, R., "Ultrasound Contrast Agents", *Current Opinion In Radiology* 3:198–207 (1991).

Schneider, et al., "Polymeric Microballoons As Ultrasound Contrast Agents Physical And Ultrasonic Properties Compared With Sonicated Albumin", *Invest. Radiol.*, 27:134–139(1992).

Schubert, K. V., et al., "Microemulsifying Fluorinated Oils With Mixtures of Fluorinated and Hydrogenated Surfactants, Colloids and Surfaces: Physicochemical and Engineering Aspects" 84:97–109 (1994).

Sehgel, et al., "Influence of Postprocessing Curves On Contrast–Echographic Imaging: Preliminary Studies", *J. Ultrasound Med.*, 14:735–740(1995).

Serratrice, G., et al., "Co–Colubilisation De Fluorocarbures Et D'Eau En Présence De Nouveaux Tensioactifs Non Ioniques Fluorés", *Journal Chim. Phys.* 87:1969–1980 (1990).

Shapiro, et al., "Intravenous Contrast Echocardiography With Use Of Sonicated Albumin In Humans: Systolic Disappearance Of Left Ventricular Contrast After Transpulmonary Transmission", *J. Am. Coll. Cardiol.*, 16:1603–1607(1990).

Smith, et al., "Left Heart Opacification With Peripheral Venous Injection Of A New Saccharide Echo Contrast Agent In Dogs", *J. Am. Coll. Cardiol.*, 13:1622–1628 (1989).

Swanson, D., et al., "Pharmaceuticals in medical Imaging, Radiopaque contrast Media, Radiopharmaceuticals, Enhancement Agents for Magnetic Resonance Imaging and Ultrasound," Ch. 22 pp 682–685 (1990).

Szönyi, F., et al., "Syntheses De Tensioactifs F–Alkyles Non Ioniques Monodisperses", *Journal of Fluorine Chemistry* 36:195–209 (1987).

Torchilin, A. Klibanov, *Critical Reviews in Therapeutic Drug Carrier Systems*, 7(4):275–307(1991).

Vygantas et al., "Octafluorocyclobutane and Other Gases for Vitreous Replacement", *Arch. Ophthalmol.*, 90:235–6 (1973).

Verescon, Christian, et al., "An Easy, Convenient Was of Describing The Stability of Fluorocarbon Emulsions", *Journal de Chimie Physique* 86:2111–2116 (1989).

Violante, M. R., et al., "Particle Stabilized Bubbles For Enhanced Organ Ultrasound Imaging", *Investigative Radiology* 26:194–200, Nov. 1991.

Widder, Donald J., et al., "Microbubbles As a Contrast Agent for Neurosonography and Ultrasound–Guided Catheter Manipulation: In Vitro Studies", *AJR* 147:347–352, Aug. 1986.

Woodle, et al., "Versatility in Lipid Compositions Showing Prolonged Circulation With Sterically Stabilized Liposomes", *Biochimica et Biophysics Acta*, 1105:193–200(1992).

Yang, et al., "Computed Tomographic Liver Enhancement with Poly(d,l–Lactide)–Microencapsulated Contrast Media," *Investigative Radiology* 29:S267–S270 (1994).

Zarif, Leila, et al, "Synergistic Stabilization of Perfluorocarbon–Pluronic F–68 Emulsion by Perfluoroalkylated Polyhydroxylated Surfactants", *Jaocks* 66:10, Oct. 1989.

Ziskin, Marvin, C., et al., "Contrast Agents For Diagnostic Ultrasound", *Investigative Radiology* 6:500–505 (1972).

Zhu, et al., "Preparation, Characterization and Properties of Polylactide (PLA)–Poly(ethylene glyco) (PEG) Copolymers: A Potential Drug Carrier", *J. Polym. Sci., Polm. Lett. Ed.*, 24:331 (1986).

MICROENCAPSULATED FLUORINATED GASES FOR USE AS IMAGING AGENTS

This application is a continuation of U.S. Ser. No. 08/745,676, filed Nov. 8, 1996, U.S. Pat. No. 5,853,698 which is a continuation of U.S. Ser. No. 08/611,248, filed Mar. 5, 1996, by Howard Bernstein, Julie Ann Straub, Henry T. Brush and Richard E. Wing entitled "Microencapsulated Fluorinated Gases for Use as Imaging Agents", now issued as U.S. Pat. No. 5,611,344.

BACKGROUND OF THE INVENTION

The present invention is generally in the area of diagnostic imaging agents, and is particularly directed to microencapsulated ultrasound imaging contrast agents.

When using ultrasound to obtain an image of the internal organs and structures of a human or animal, ultrasound waves, waves of sound energy at a frequency above that discernable by the human ear, are reflected as they pass through the body. Different types of body tissue reflect the ultrasound waves differently and the reflections that are produced by the ultrasound waves reflecting off different internal structures are detected and converted electronically into a visual display.

For some medical conditions, obtaining a useful image of the organ or structure of interest is especially difficult because the details of the structure are not adequately discernible from the surrounding tissue in an ultrasound image produced by the reflection of ultrasound waves absent a contrast-enhancing agent. Detection and observation of certain physiological and pathological conditions may be substantially improved by enhancing the contrast in an ultrasound image by infusing an agent into an organ or other structure or interest. In other cases, detection of the movement of the contrast-enhancing agent itself is particularly important. For example, a distinct blood flow pattern that is known to result from particular cardiovascular abnormalities may only be discernible by infusing a contrasting agent into the bloodstream and observing the dynamics of the blood flow.

Materials that are useful as ultrasound contrast agents operate by having an effect on ultrasound waves as they pass through the body and are reflected to create the image from which a medical diagnosis is made. Different types of substances affect ultrasound waves in different ways and to varying degrees. Moreover, certain of the effects caused by contrast-enhancing agents are more readily measured and observed than others. In selecting an ideal composition for a contrast-enhancing agent, one would prefer the substance that has the most dramatic effect on the ultrasound wave as it passed through the body. Also, the effect on the ultrasound wave should be easily measured. There are three main contrast-enhancing effects which can be seen in an ultrasound image: backscatter, beam attenuation, and speed of sound differential.

BACKSCATTER: When an ultrasound wave that is passing through the body encounters a structure, such as an organ or other body tissue, the structure reflects a portion of the ultrasound wave. Different structures within the body reflect ultrasound energy in different ways and in varying strengths. This reflected energy is detected and used to generate an image of the structures through which the ultrasound wave has passed. The term "backscatter" refers to the phenomena in which ultrasound energy is scattered back towards the source by a substance with certain physical properties.

It has long been recognized that the contrast observed in an ultrasound image may be enhanced by the presence of substances known to cause a large amount of backscatter. When such a substance is administered to a distinct part of the body, the contrast between the ultrasound image of this part of the body and the surrounding tissues not containing the substance is enhanced. It is well understood that, due to their physical properties, different substances cause backscatter in varying degrees. Accordingly, the search for contrast-enhancing agents has focused on substances that are stable and non-toxic and that exhibit the maximum amount of backscatter.

The capability of a substance to cause backscatter of ultrasound energy depends on characteristics of the substance such as its ability to be compressed. When examining different substances, it is useful to compare one particular measure of the ability of a substance to cause backscatter known as the "scattering cross-section." The scattering cross-section of a particular substance is proportional to the radius of the scatterer, and also depends on the wavelength of the ultrasound energy and on other physical properties of the substance, J. Ophir and K. J. Parker, *Contrast Agents in Diagnostic Ultrasound*, Ultrasound in Medicine & Biology, vol. IS, n. 4, p. 319, 323 (1989).

In evaluating the utility of different substances as image contrasting agents, one can calculate which agents should have the higher scattering cross-section and, accordingly, which agents should provide the greatest contrast in an ultrasound image. It can be assumed that the compressibility of a solid particle is much less than that of the surrounding medium and that the density of the particle is much greater. Using this assumption, the scattering cross section of a solid particle contrast-enhancing agent has been estimated as 1.75. Ophir and Parker, supra, at 325. For a pure liquid scatterer, the adiabatic compressibility and density of the scatterer and the surrounding medium are likely to be approximately equal, which would yield the result that liquids would have a scattering cross-section of zero. However, liquids may exhibit some backscatter if large volumes of a liquid agent are present. For example, if a liquid agent passes from a very small vessel to a very large one such that the liquid occupies substantially all of the vessel, the liquid may exhibit measurable backscatter. Nevertheless, it is appreciated by those skilled in the art that pure liquids are relatively inefficient scatterers compared to free gas microbubbles.

BEAM ATTENUATION: Another effect which can be observed from the presence of certain solid contrast-enhancing agents, is the attenuation of the ultrasound wave. Image contrast has been observed in conventional imaging due to localized attenuation differences between certain tissue types. K. J. Parker and R. C. Wang, "Measurement of Ultrasonic Attenuation Within Regions selected from B-Scan Images," *IEEE Trans. Biomed. Enar. BME* 30(8), p. 431–37 (1983); K. J. Parker, R. C. Wang, and R. M. Lerner, "Attenuation of Ultrasound Magnitude and Frequency Dependence for Tissue Characterization," Radiology, 153 (3), p. 785–88 (1984). It has been hypothesized that measurements of the attenuation of a region of tissue taken before and after infusion of an agent may yield an enhanced image. However, techniques based on attenuation contrast as a means to measure the contrast enhancement of a liquid agent are not well-developed and, even if fully developed, may suffer from limitations as to the internal organs or structures with which this technique can be used. For example, it is unlikely that a loss of attenuation due to liquid contrast agents could be observed in the image of the cardiovascular system because of the high volume of liquid contrast agent that would need to be present in a given vessel before a substantial difference in attenuation could be measured.

The absorption of energy by the particles occurs by a mechanism referred to as "relative motion." The change in attenuation caused by relative motion can be shown to increase linearly with particle concentration and as the square of the density difference between the particles and the surrounding medium. K. J. Parker, et al., "A Particulate Contrast Agent with Potential for Ultrasound Imaging of Liver," *Ultrasound in Medicine & Biology*, Vol. 13, No. 9, p. 555, 561 (1987). Therefore, where substantial accumulation of solid particles occurs, attenuation contrast may be a viable mechanism for observing image contrast enhancement although the effect is of much smaller magnitude than the backscatter phenomenon and would appear to be of little use in cardiovascular diagnoses.

SPEED OF SOUND DIFFERENTIAL: An additional technique to enhance contrast in an ultrasound image has been proposed based on the fact that the speed of sound varies depending on the media through which it travels. Therefore, if a large enough volume of an agent, through which the speed of sound is different than the surrounding tissue, can be infused into a target area, the difference in the speed of sound through the target area may be measurable.

In summary, diagnostic ultrasound is a powerful, non-invasive tool that can be used to obtain information on the internal organs of the body. The advent of grey scale imaging and color Doppler have greatly advanced the scope and resolution of the technique. Although techniques for carrying out diagnostic ultrasound have improved significantly, and for making and using contrast agents, there is still a need to enhance the resolution of the imaging for cardiac perfusion and cardiac chambers, solid organs, renal perfusion; solid organ perfusion; and Doppler signals of blood velocity and flow direction during real-time imaging.

A variety of natural and synthetic polymers have been used to encapsulate imaging contrast agents, such as air. Schneider et al., *Invest. Radiol.*, Vol. 27, pp. 134–139 (1992) describes three micron, air-filled polymeric particles. These particles were reported to be stable in plasma and under applied pressure. However, at 2.5 MHz, their echogenicity was low. Another type of microbubble suspension has been obtained from sonicated albumin. Feinstein et al., *J. Am. Coll. Cardiol.*, Vol. 11, pp. 59–65 (1988). Feinstein describes the preparation of microbubbles that are appropriately sized for transpulmonary passage with excellent stability in vitro. However, these microbubbles are short-lived in vivo, having a hall life on the order of a few seconds (which is approximately equal to one circulation pass) because of their instability under pressure. Gottlieb, S. et al., *J. Am. Soc. Echo.*, Vol. 3, pp. 328 (1990), Abstract; and Shapiro, J. R. et al., *J. Am. Coll. Cardiol.*, Vol. 16, pp. 1603–1607 (1990). Gelatin-encapsulated air bubbles have been described by Carroll et al. (Carroll, B. A. et al., *Invest. Radiol.*, Vol. 15, pp. 260–266 (1980), and Carroll, B. A. et al., *Radiology*, Vol. 143, pp. 747–750 (1982)), but due to their large sizes (12 and 80 $\mu$m) they would not be likely to pass through pulmonary capillaries. Gelatin-encapsulated microbubbles have also been described in PCT/US80/00502 by Rasor Associates, Inc. These are formed by "coalescing" the gelatin.

Microbubbles stabilized by microcrystals of galactose (SHU 454 and SHU 508) have also been reported by Fritzch et al. Fritzsch, T. et al., *Invest. Radiol.* Vol. 23 (Suppl 1), pp. 302–305 (1988); and Fritzsch, T. et al., *Invest. Radiol.*, Vol. 25 (Suppl 1), 160–161 (1990). The microbubbles last up to 15 minutes in vitro but less than 20 seconds in vivo. Rovai, D. et al., *J. Am. Coll. Cardiol.*, Vol. 10, pp. 125–134 (1987); and Smith, M. et al., *J. Am. Coll. Cardiol.*, Vol. 13, pp. 1622–1628 (1989).

European Patent Application No. 90901933.5 by Schering Aktiengesellschaft discloses the preparation and use of microencapsulated gas or volatile liquids for ultrasound imaging, where the microcapsules are formed of synthetic polymers or polysaccharides. European Patent Application No. 91810366.4 by Sintetica S. A. (0 458 745 A1) discloses air or gas microballoons bounded by an interfacially deposited polymer membrane that can be dispersed in an aqueous carrier for injection into a host animal or for oral, rectal, or urethral administration, for therapeutic or diagnostic purposes. WO 92/18164 by Delta Biotechnology Limited describes the preparation of microparticles by spray drying under very controlled conditions as to temperature, rate of spraying, particle size, and driving conditions, of an aqueous protein solution to form hollow spheres having gas entrapped therein, for use in imaging WO 93/25242 describes the synthesis of microparticles for ultrasonic imaging consisting of a gas contained within a shell of polycyanoacrylate or polyester. WO 92/21382 discloses the fabrication of microparticle contrast agents which include a covalently bonded matrix containing a gas, wherein the matrix is a carbohydrate. U.S. Pat. Nos. 5,334,381, 5,123,414 and 5,352,435 to Unger describe liposomes for use as ultrasound contrast agents, which include gases, gas precursors, such as a pH activated or photo-activated gaseous precursor, as well as other liquid or solid contrast enhancing agents.

U.S. Pat. No. 5,393,524 to Quay discloses the use of agents, including fluorocarbons, for enhancing the contrast in an ultrasound image. The agents consist of extremely small bubbles, or microbubbles, of selected gases, which exhibit long life spans in solution and are small enough to traverse the lungs, enabling their use in ultrasound imaging of the cardiovascular system and other vital organs. WO95/23615 by Nycomed discloses microcapsules for imaging which are formed by coacervation of a solution, for example, a protein solution, containing a perfluorocarbon. PCT/US94/08416 by Massachusetts Institute of Technology discloses microparticles formed of polyethylene glycol-poly (lactide-co-glycolide) block polymers having imaging agents encapsulated therein, including gases such as air and perfluorocarbons. As described in WO94/16739 by Sonus Pharmaceuticals, Inc., while solids and liquids reflect sound to a similar degree, gases are known to be more efficient and are the preferred media for use as ultrasound contrast agents. In fact, as shown by example 12 of the Sonus PCT application, protein microcapsules were dismissed as raising safety concerns (as well as efficacy issues) when administered to mini-pigs, as compared to emulsions or colloidal suspensions.

In all of these cases it is desirable to enhance the echogenicity of the imaging agent, in conjunction with enhancing or maintainting the stability and case of manufacturing of the imaging agent.

It is therefore an object of the present invention to provide microparticles made from synthetic polymers with significantly enhanced echogenicity.

SUMMARY OF THE INVENTION

It has been discovered that the incorporation of fluorinated gases, especially perfluorocarbons such as octafluoropropane, into synthetic polymeric microparticles, especially highly porous sponge-like microspheres, have significantly enhanced echogenicity as compared with microspheres encapsulating air. The microencapsulated fluorinated gas is manufactured with a diameter suitable for the targeted tissue to be imaged, for example, with a diameter of between 0.5 and 8 microns for intravascular administration, and a diameter of between 0.5 and 5 mm for oral administration for imaging of the gastrointestinal tract or other lumens.

DEATILED DESCRIPTION OF THE INVENTION

Methods are provided for the synthesis of polymeric delivery systems consisting of synthetic polymeric microparticles which contain fluorinated gases, especially perfluorocarbons. The microparticles are useful in a variety of diagnostic ultrasound imaging applications, particularly in ultrasound procedures such as blood vessel imaging and echocardiography. The incorporation of a fluorinated gas significantly increases the echogenicity as compared with the same synthetic polymeric microparticles incorporating air.

Processes and Reagents for Making Microparticles

As used herein, the term microparticle includes microspheres and microcapsules, as well as microparticles, unless otherwise specified. Microparticles may or may not be spherical in shape. Microcapsules are defined as microparticles having an outer polymer shell surrounding a core of another material, in this case, a gas. Microspheres are generally solid polymeric spheres, which can include a honeycombed structure formed by pores through the polymer which are filled with a gas for imaging purposes, as described below.

Polymers

Both non-biodegradable and biodegradable matrices can be used for delivery of fluorinated gases, although biodegradable matrices are preferred, particularly for intravenous injection. Nonerodible polymers may be used for oral administration. Synthetic polymers are preferred due to more reproducible synthesis and degradation. The polymer is selected based on the time required for in vivo stability, i.e., that time required for distribution to the site where imaging is desired, and the time required for imaging. In one embodiment, microparticles with an in vivo stability of between about 20 to 30 minutes or more may be fabricated, for example for use in applications such as echocardiography, neurosonography, hysterosalpingography, and diagnostic procedures on solid organs. The in vivo stability of the contrast agent-encapsulated microparticles can be adjusted during the production by using polymers such as polylactide co-glycolide copolymerized with polyethylene glycol (PEG). PEG if exposed on the external surface may elongate the time these materials circulate since it is very hydrophilic.

Representative synthetic polymers are: poly(hydroxy acids) such as poly(lactic acid), poly(glycolic acid), and poly(lactic acid-co-glycolic acid), polyglycolides, polylactides, polylactide co-glycolide copolymers and blends, polyanhydrides, polyorthoesters, polyamides, polycarbonates, polyalkylenes such as polyethylene and polypropylene, polyalkylene alycols such as poly(ethylene glycol), polyalkylene oxides such as poly(ethylene oxide), polyalkylene terepthalates such as poly(ethylene terephthlalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred non-biodegradable polymers include ethylene vinyl acetate, poly(meth)acrylic acid, polyamides, copolymers and mixture thereof.

Examples of preferred biodegradable polymers include polymers of hydroxy acids such as lactic acid and glycolic acid polylactide, polyglycolide, polylactide co-glycolide, and copolymers with PEG, polyanhydrides, poly(ortho) esters, polyurethanes, poly(butyric acid), poly(valeric acid), and poly(lactide-co-caprolactone). In general, these materials degrade it vivo by both non-enzymatic and enzymatic hydrolysis, and by surface or bulk erosion.

Bioadhesive polymers of particular interest for use in imaging of mucosal surfaces, as in the gastrointestinal tract, include polyanhydrides, polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Solvents

As defined herein, the polymer solvent is an organic solvent that is volatile or has a relatively low boiling point or can be removed under vacuum and which is acceptable for administration to humans in trace amounts, such as methylene chloride. Other solvents, such as ethyl acetate, acetone, acetonitrile, tetrahydrofuran (THF), acetic acid, DMSO and chloroform also may be utilized, or combinations thereof. In general, the polymer is dissolved in the solvent to form a polymer solution having a concentration of between 0.1 and 60% weight to volume (w/v), more preferably between 0.5 and 30%.

Fluorinated Gases

Any biocompatible or pharmacologically acceptable fluorinated gas can be incorporated into the microparticles. The term gas refers to any compound which is a gas or capable of forming a gas at the temperature at which imaging is being performed. The gas may be composed of a single compound or a mixture of compounds. Perfluorocarbon gases are preferred. Examples of gases include $CF_4$, $C_2F_6$, $C_3F_8$, $C_4F_8$, $SF_6$, $C_2F_4$, and $C_3F_6$. Perfluoropropane is particularly preferred because it provides an insoluble gas that will not condense at the temperature of use and is pharmacologically acceptable.

Microparticles and Methods for Manufacture Thereof

In the most preferred embodiment, the microparticles are produced by spray drying. Other techniques can be used, such as solvent extraction, hot melt encapsulation, and solvent evaporation, as discussed below.

In a preferred embodiment, the gas is then replaced by applying a stream of the desired gas to, or pulling a vacuum on, the microspheres to remove the encapsulated gas, then filling with the desired gas.

a. Solvent Evaporation. In this method the polymer is dissolved in a volatile organic solvent such as methylene chloride. A pore forming agent as a solid or in an aqueous solution may be added to the solution. The mixture is sonicated or homogenised and the resulting dispersion or emulsion is added to an aqueous solution that contains a surface active agent such as TWEEN™ 20, TWEEN™ 80, PEG or poly(vinyl alcohol) and homogenised to form an emulsion. The resulting emulsion is stirred until most of the organic solvent evaporates, leaving microspheres. Several different polymer concentrations can be used (0.05–0.60 g/ml). Microspheres with different sizes (1–1000 microns) and morphologies can be obtained by this method. This method is useful for relatively stable polymers like polyesters and polystyrene.

Solvent evaporation is described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984), the teachings of which are incorporated herein.

However, labile polymers, such as polyanhydrides, may degrade during the fabrication process due to the presence of water. For these polymers, the following two methods, which are performed in completely organic solvents, are more useful.

Hot Melt Microencapsulation. In this method, the polymer is first melted and then mixed with the solid particles of the pore forming agent. The mixture is suspended in a non-miscible solvent (like silicon oil), and, while stirring continuously, heated to 5° C. above the melting point of the polymer. Once the emulsion is stabilized, it is cooled until the polymer particles solidify. The resulting microspheres are washed by decantation with a polymer non-solvent such as petroleum ether to give a free-flowing powder. Microspheres with sizes between one to 1000 microns can be obtained with this method. The external surfaces of spheres prepared with this technique are usually smooth and dense. This procedure is used to prepare microspheres made of polyesters and polyanhydrides. However, this method is limited to polymers with molecular weights between 1000–50,000.

Hot-melt microencapsulation is described by E. Mathiowitz, et al., *Reactive Polymers*, 6, 275 (1987), the teachings of which are incorporated herein. Polyanhydrides, for example, made of bis-carboxyphenoxypropane and sebacic acid with molar ratio of 20:80 (P(CPP-SA) 20:80) (Mw 20,000), can be prepared by hot-melt microencapsulation or for example, poly(fumaric-co-sebacic) (20:80) (Mw 15,000) blank microspheres, can be prepared by hot-melt microencapsulation.

c. Solvent Removal. This technique was primarily designed for polyanhydrides. In this method, the pore forming agent is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microspheres from polymers with high melting points and different molecular weights. The external morphology of spheres produced with this technique is highly dependent on the type of polymer used.

d. Spray Drying of Microparticles. Microparticles can be produced by spray drying by dissolving a biocompatible polymer in an appropriate solvent, dispersing a pore forming agent into the polymer solution, and then spray drying the polymer solution, to form microparticles. As defined herein, the process of "spray drying" a solution of a polymer and a pore forming agent refers to a process wherein the solution is atomized to form a fine mist and dried by direct contact with hot carrier gases. Using spray drying apparatus available in the art, the polymer solution may be delivered through the inlet port of the spray drier, passed through a tube within the drier and then atomized through the outlet port. The temperature may be varied depending on the gas or polymer used. The temperature of the inlet and outlet ports can be controlled to produce the desired products.

The size of the particulates of polymer solution is a function of the nozzle used to spray the polymer solution, nozzle pressure, the flow rate, the polymer used, the polymer concentration, the type of solvent and the temperature of spraying (both inlet and outlet temperature) and the molecular weight. Generally, the higher the molecular weight, the larger the capsule size, assuming the concentration is the same. Typical process parameters for spray drying are as follows: polymer concentration=0.005–0.10 g/ml, inlet temperature=30–200° C., outlet temperature=20–100° C., polymer flow rate=5–200 ml/min., and nozzle diameter= 0.2–4 mm ID. Microspheres ranging in diameter between one and ten microns can be obtained with a morphology which depends on the selection of polymer, concentration, molecular weight and spray flow.

e. Hydrogel Microspheres. Microspheres made of gel-type polymers, such as polyphosphazene or polymethylmethacrylate, are produced by dissolving the polymer in an aqueous solution, suspending the pore forming agent in the mixture and extruding through a microdroplet forming device, producing microdroplets which fall into a hardening bath consisting of an oppositely charged ion or polyelectrolyte solution. that is slowly stirred. The advantage of these systems is the ability to further modify the surface of the microspheres by coating them with polycationic polymers, like polylysine after fabrication. Microsphere particles are controlled by using various size extruders.

Additives to Facilitate Microparticulate Formation

A variety of surfactants may be added during the synthesis of the image agent-containing microparticles. Exemplary emulsifiers or surfactants which may be used (0.1–5% by weight) include most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxpropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose.

Other emulsifiers include natural and synthetic forms of bile salts or bile acids, both conjugated with amino acids and unconjugated such as taurodeoxycholate, and cholic acid.

This can, for example, stabilize microbubbles generated prior to spray-drying.

Pore forming agents can be included in an amount of between 0.01% and 75% weight to volume, to increase pore formation. For example, in solvent evaporation, a pore forming agent such as a volatile salt, for example, ammonium bicarbonate, ammonium acetate, ammonium chloride or ammonium benzoate or other lyophilizable salt, is first dissolved in water. The solution containing the pore forming agent is then emulsified with the polymer solution to create droplets of the pore forming agent in the polymer. This emulsion is then spray dried or taken through a solvent evaporation/extraction process. After the polymer is precipitated, the hardened microspheres are frozen and lyophilized to remove the pore forming agents.

Microparticle Size

In a preferred embodiment for the preparation of injectable microparticles capable of passing through the pulmonary capillary bed, the microparticles should have a diameter of between approximately one and ten microns. Larger microparticles may clog the pulmonary bed, and smaller microparticles may not provide sufficient echogenicity. Larger microparticles are useful for administration by routes other than injection, for example oral (for evaluation of the gastrointestinal tract), application to other mucosal surfaces (rectal, vaginal, oral, nasal) or by inhalation. The preferred particle size for oral administration is about 0.5 microns and 5 mm. Useful pharmaceutically acceptable carriers include saline containing glycerol and TWEEN™ 20 and isotonic mannitol containing TWEEN™ 20. Particle size analysis can be performed on a Coulter counter by light microscopy, scanning electron microscopy, or transmittance electron microscopy.

Targeting

The microparticles can be targeted specifically or non-specifically through the selection of the polymer forming the microparticle, the size of the microparticle, and/or incorporation or attachment of a ligand to the microparticles. For example, biologically active molecules, or molecules affecting the charge, lipophilicity or hydrophilicity of the particle, may be attached to the surface of the microparticle. Additionally, molecules may be attached to the microparticles which minimize tissue adhesion, or which facilitate specific targeting of the microspheres in vivo. Representative targeting molecules include antibodies, lectins, and other molecules which are specifically bound by receptors on the surfaces of cells of a particular type.

Inhibition of Uptake by the RES

Uptake and removal of the microparticles can also be minimized through the selection of the polymer and/or incorporation or coupling of molecules which minimize adhesion or uptake. For example, tissue adhesion by the microparticle can be minimized by covalently binding poly (alkylene glycol) moieties to the surface of the microparticle. The surface poly(alkylene glycol) moieties have a high affinity for water that reduces protein adsorption onto the surface of the particle. The recognition and uptake of the microparticle by the reticulo-endothelial system (RES) is therefore reduced.

For example, the terminal hydroxyl group of the poly (alkylene glycol) can be used to covalently attach biologically active molecules, or molecules affecting the charge, lipophilicity or hydrophilicity of the particle, onto the surface of the microparticle. Methods available in the art can be used to attach any of a wide range of ligands to the microparticles to enhance the delivery properties, the stability or other properties of the microparticles in vivo.

Diagnostic Applications

Microparticles are typically combined with a pharmaceutically acceptable carrier such as phosphate buffered saline or saline or mannitol, then an effective amount for detection administered to a patient using an appropriate route, typically by injection into a blood vessel (i.v.) or orally Microparticles containing an encapsulated imaging agent may be used in vascular imaging, as well as in applications to detect liver and renal diseases, in cardiology applications, in detecting and characterizing tumor masses and tissues, and in measuring peripheral blood velocity. The microparticles also can be linked with ligands that minimize tissue adhesion or that target the microparticles to specific regions of the body in vivo as described above.

The methods and compositions described above will be further understood with reference to the following non-limiting examples.

EXAMPLE 1

Preparation of Air Filled PEG-PLGA Microspheres 6.0 grams of PEG-PLGA (75:25) (120,000 Da mw) was dissolved in 400 ml methylene chloride. 6.7 ml of water was added to the polymer and the polymer/water mixture was homogenised at 10,000 RPM for 1 minute using a Virtis homogenizer. The solution was pumped at a flowrate of 20 ml/min using a peristaltic pump and sprayed dried using a Bucchi Lab spray dryer. The inlet temperature was 50° C. and the outlet temperature was 30° C. The microsphere powder was collected and lyophilized at ambient temperature for 48 hours. The particle diameters range from 1–10 microns when sized on a coulter counter with a number average mean of 2.0 microns and volume average mean of 4.5 microns. Scanning electron microscopy demonstrated the particles to be generally spherical with smooth surfaces and occasional surface crenulations. Transmission electron microscopy revealed the particles to be mixture of microcapsule like particulates and sponge like particulates.

EXAMPLE 2

Preparation of Air Filled PEG-PLGA Microspheres 7.1 grams of PEG-PLGA (75:25) (120,000 Da mw) was dissolved in 320 ml methylene chloride. 11 ml of 0.74 g/ml ammonia acetate was added to the polymer and the polymer/ammonia acetate mixture was homogenised at 16,000 RPM for 1 minute using a Virtis homogeniser. The solution was pumped at a flowrate of 20 ml/min using a peristaltic pump and sprayed dried using a Bucchi Lab spray dryer. The inlet temperature was 32° C. and the outlet temperature was 19° C. The microsphere powder was collected and lyophilized at ambient temperature for 48 hours. The particle diameters ranged from 1–10 microns when sized on a Coulter counter with a number average mean of 1.8 microns and volume average mean of 5.1 microns. Scanning electron microscopy demonstrated the particles to be generally spherical with smooth surfaces and occasional surface crenulations.

EXAMPLE 3

Preparation of Octafluoropropane Filled PEG-PLGA Microspheres

The microspheres prepared as described in Example 2 were dispersed in 54 mg mannitol/ml and 0.5% PLURONIC™ F127. The dispersion was aliquoted into 5 ml vials. The vials were frozen at –80° C. and lyophilized overnight.

EXAMPLE 4

Preparation of Octafluoropropane Filled PLGA Microspheres 7.4 grams of PLGA (75:25) (120,000 Da mw) was dissolved in 360 ml methylene chloride. 7.3 ml of a 0.74 g ammonia acetate/ml was added to the polymer and the polymer/anmmonia acetate solution was homogenised at 16,000 RPM for 1 minute using a Virtis homogeniser. The solution was pumped at a flowrate of 20 ml/min using a peristaltic pump and sprayed dried using a Bucchi Lab spray dryer. The inlet temperature was 32° C. and the outlet temperature was 20° C. The microsphere powder was collected and lyophilized at ambient temperature for 48 hours. The particle diameters ranged from 1–10 microns when sized on a Coulter counter with a number average mean of 2.0 microns and a volume average mean of 5.2 microns. Scanning electron microscopy demonstrated the particles to be generally spherical with smooth surfaces and occasional surface crenulations. The microspheres prepared in Example 2 were dispersed in 54 mg mannitol/ml and 0.5% PLURONIC™ F127. The dispersion was aliquoted into 5 ml vials. The vials were frozen at −80° C. and lyophilized overnight. The vials were filled with octofluoroproprane at a pressure of 10 psig and purged continuously under the gas for three minutes. After this point the vials were stored at −20° C. for 24 hours and their stored at 4° C. until used.

EXAMPLE 5

In vivo Evaluation of Microencapsulated Air

Male New Zealand rabbits (2–2.5 kg) were fasted overnight. The animals were anesthetized with ketamine (100 mg/mL, 0.7 mL) and rompum (20 mg/mL, 0.5 mL). The dosage form was administered intravenously over approximately 5 seconds through a catheter located in the left marginal ear vein. After administration, the catheter was flushed with one mL of normal saline. All vials were equilibrated to room temperature prior to reconstitution. The dosage form was reconstituted not more than 2 minutes prior to injection. The reconstitution procedure consisted of adding 1 mL of water to the vial, allowing the gas pressure in the vial to equilibrate to atmospheric by pushing out the plunger on the 5 mL syringe, withdrawing the syringe needle and swirling the vial until all of the lyophile had dissolved. Ultrasonic imaging of the heart was performed with an ATL HDI 3000 clinical ultrasound imaging device equipped with a C7-4 high resolution transducer. The transmit intensity was such that the Tls was 0.3 and the MI was 0.8. The frame rate was 39 Hz, the depth was set 9.7 cm, the image was processed with Map 6 and the dynamic range was 55 dB. Imaging was performed before, during and after administration of the agents. The heart was imaged in B-mode, and the machine settings were adjusted to make the chambers as anechoic as possible. The complete set of images was recorded on sVHS tape, with imaging continuing until no further signal was detected.

The microspheres prepared in example 1 (Lot 943-110-1) were administered to a rabbit (#13) at a dose of 26.2 mg/kg. Within 10 seconds, a wide stream of echogenic material was observed flowing into and filling the right atrium. The stream passed into the right atrium and filled the right ventricle. Visually, the intensity in the two chambers appeared equal. No echogenicity was observed flowing into the left ventricle. The enhancement in the light atrium and the right ventricle lasted for approximately 30 seconds.

EXAMPLE 6

In vivo Evaluation of Microencapsulated Perfluorocarbon Particles

The microspheres prepared in example 3 (Lot #952-7-3) was administered to a rabbit (#18) at a dose of 24 mg/kg. The intensity in the right ventricle increased followed by increasing intensity in the left ventricle. Excellent chamber opacification was observed. After 2.5 minutes, the chamber intensities returned to baseline.

The microspheres prepared in example #4 (Lot #952-49-1) was administered to a rabbit (#19) at a dose of 22 mg/kg. The intensity in the right ventricle increased followed by increasing intensity in the left ventricle. Excellent chamber opacification was observed. The chamber intensities returned to baseline by 2 minutes.

These examples demonstrate excellent chamber opacification.

Similar studies have been conducted with different fluorinated gases, sulfur hexafluoride and hexafluorocylclobutane.

Modifications and variations of the present invention will be obvious to those skilled in the art from the foregoing detailed description. Such modifications and variations are intended to come within the scope of the following claims.

We claim:

1. A method for enhancing the echogenicity of a porous microparticle formed of air and a synthetic biocompatible polymer, wherein the polymer is soluble in an organic solvent, comprising removing the air through the pores of the microparticle and replacing the air with a fluorinated gas in an amount effective to image the microparticle after administration to a patient.

2. The method of claim 1 wherein the gas is a perfluorocarbon.

3. The method of claim 1 wherein the gas is selected from the group consisting of $CF_4$, $C_2F_6$, $C_3F_8$, $C_4F_8$, $SF_6$, $C_2F_4$, and $C_3F_6$.

4. The method of claim 3 wherein the gas is octafluoropropane.

5. The method of claim 1 wherein the microparticle is a microcapsule.

6. The method of claim 1 wherein the microparticle is a microsphere having voids therein, wherein the voids are formed by incorporating into a solution of the polymer an effective amount of a volatile salt, removing the polymer solvent, and then removing the volatile salt by lyophilization.

7. The method of claim 1 wherein the microparticle is formed of a bioadhesive synthetic polymer.

8. The method of claim 1 wherein the microparticle is formed of a synthetic polymer selected from the group consisting of poly(hydroxy acids), polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly (valeric acid), and poly(lactide-co-caprolactone), ethylene vinyl acetate, copolymers and blends thereof.

9. A composition for administration to a patient for imaging with ultrasound comprising a biocompatible porous polymeric microparticle, and a pharmaceutically acceptable carrier for administration of the microparticles to a patient, wherein the microparticle is formed of air and a synthetic biocompatible polymer, other than a polyethylene glycol and poly(lactic acid-co-glycolide) copolymer, wherein the polymer is soluble in an organic solvent, wherein the air is removed through the pores and replaced with an effective amount of a fluorinated gas for enhanced imaging by ultrasound after administration to a patient as compared with the microparticle incorporating therein an equivalent volume of air.

10. The composition of claim 9 wherein the gas is a perfluorocarbon.

11. The composition of claim 9 wherein the gas is selected from the group consisting of $CF_4$, $C_2F_6$, $C_3F_8$, $C_4F_8$, $SF_6$, $C_2F_4$, and $C_3F_6$.

12. The composition of claim 11 wherein the perfluorocarbon is octafluoropropane.

13. The composition of claim 9 wherein the microparticle is a microcapsule.

14. The composition of claim 9 wherein the microparticle is a microsphere having voids therein, wherein the voids are formed by incorporating into a solution of the biocompatible polymer an effective amount of a volatile salt, removing the polymer solvent, and then removing the volatile salt by lyophilization.

15. The composition of claim 9 wherein the microparticle is formed of a bioadhesive synthetic polymer.

16. The composition of claim 9 wherein the microparticle is formed of a synthetic polymer selected from the group consisting of poly(hydroxy acids) other than a polyethylene glycol and poly(lactic acid-co-glycolide) copolymer, polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly (lactide-co-caprolactone), ethylene vinyl acetate, copolymers and blends thereof.

17. The composition of claim 9 wherein the microparticle is formed by incorporating into a solution of the polymer an effective amount of a volatile salt, then removing the polymer solvent and the volatile salt to form the porous microparticle.

18. The composition of claim 17 wherein the volatile salt is selected from the group consisting of ammonium bicarbonate, ammonium acetate, ammonium chloride, ammonium benzoate and mixtures thereof.

19. The composition of claim 17 wherein the volatile salt is incorporated into the polymer solution at a ratio of between 0.01% and 75% weight to volume.

20. The composition of claim 17 wherein the volatile salt is dissolved in an aqueous solution, emulsified with the polymer solution to create droplets of the pore forming agent in the polymer, and then spray dried.

21. The composition of claim 20 wherein after the polymer is precipitated, the pore forming agents are removed by freezing and lyophilizing the precipitated polymer.

* * * * *